United States Patent [19]

Behnke

[11] 4,195,636

[45] Apr. 1, 1980

[54] ARM FLESH INJECTION SITE CLAMP

[76] Inventor: Robert C. Behnke, 1917 Michigan St., Oshkosh, Wis. 54901

[21] Appl. No.: 890,696

[22] Filed: Mar. 27, 1978

[51] Int. Cl.² .............................................. A61B 17/00
[52] U.S. Cl. ..................................................... 128/346
[58] Field of Search ............... 128/346, 327, 325, 215; 24/261 C, 262 GC

[56] References Cited

U.S. PATENT DOCUMENTS

| 2,704,071 | 3/1955 | Becker | 128/215 |
| 3,463,157 | 8/1969 | Hunt | 128/325 |
| 3,760,803 | 9/1973 | Boothby | 128/346 X |

*Primary Examiner*—Stephen C. Pellegrino

*Attorney, Agent, or Firm*—Clarence A. O'Brien; Harvey B. Jacobson

[57] ABSTRACT

A pair of generally semi-circular jaws are provided opening toward each other, including first and second pairs of corresponding ends and provided for clampingly embracing an arm portion therebetween. The first pair of ends of the jaws terminate in a pair of generally parallel arm portions extending outward therefrom in a direction extending away from the second pair of corresponding ends of the jaws and spring structure operatively interconnects the outer ends of the arms yieldingly biasing the latter in directions to swing the jaws toward each other. The second pair of ends of the jaws include outwardly curving terminal ends for gently "pinching" an arm injection site therebetween.

4 Claims, 4 Drawing Figures

ARM FLESH INJECTION SITE CLAMP

BACKGROUND OF THE INVENTION

There are many persons who must give themselves medicinal injections. Some of these persons include diabetics and some diabetics as well as other persons who must give themselves medicinal injections have only one hand. Further, even "controlled" diabetics occasionally experience the need for insulin injections at times when other persons accustomed to effecting the insulin injections are not present and there are, accordingly, many instances when it is necessary that a person give himself a needed medicinal injection.

In order to assist these persons in enabling them to give themselves the required medicinal injections, various forms of skin and/or flesh clamps have been heretofore designed. Such clamps are designed to lightly "pinch" and thus distend the proposed injection site, but most of these clamps are either not operative in the desired manner or are not readily usable by all persons who may wish to give themselves medicinal injections. Examples of previously known forms of clamps designed to facilitate persons in giving themselves medicinal injections as well as other devices including some of the general structural and operational features of the instant invention are disclosed in U.S. Pat. Nos. 1,824,516, 2,704,071, 2,847,014, 3,760,803 and 3,827,438.

BRIEF DESCRIPTION OF THE INVENTION

The injection site clamp of the instant invention is constructed of a single piece of spring-type heavy gauge wire and includes a pair of generally semi-circular jaws opening toward each other, including first and second pairs of adjacent corresponding ends and adapted to clampingly embrace an arm portion therebetween. The first pair of corresponding jaw ends terminate in a pair of generally parallel integral arm portions extending outward in a direction away from the second pair of corresponding ends of the jaws and the outer ends of the arms are interconnected by means of an integral curved connecting portion and the curved connecting portion serves to yieldingly bias the ends of the arms adjacent the semi-circular jaws in directions to swing the jaws toward each other for clampingly engaging an arm therebetween.

The ends of the semi-circular jaws remote from the arms include reversely bent outwardly directed terminal ends and the terminal ends are covered with a plastic coating.

The main object of this invention is to provide a clamp which may be utilized by persons required to give themselves medicinal injections and for the purpose of preparing an arm portion as an injection site.

Another object of this invention is to provide a clamp which may also be utilized to prepare other fleshly portions of a person for receiving a medicinal injection.

Still another object of this invention is to provide a clamp in accordance with the preceding objects which includes minimal area contact adjacent the desired injection site whereby the injection site will be maintained substantially fully exposed for receiving a hypodermic needle from various different directions.

Another important object of this invention is to provide a clamp which will be capable of adapting to arms of different circumference.

Still another object of this invention is to provide an injection site clamp constructed in a manner whereby it may be readily applied to various injection site areas including areas of the arm, leg, stomach or buttocks.

A further important object of this invention is to provide an injection site clamp constructed in a manner whereby the possibility of contamination of the intended injection site by the clamp is maintained extremely remote.

A final object of this invention to be specifically enumerated herein is to provide an injection site clamp in accordance with the preceding objects and which will conform to conventional forms of manufacture, be of simple construction and easy to use so as to provide a device that will be economical feasible, long lasting and relatively trouble-free in operation.

These together with other objects and advantages which will become subsequently apparent reside in the details of construction and operation as more fully hereinafter described and claimed, reference being had to the accompanying drawings forming a part thereof, wherein like numerals refer to like parts throughout.

DETAILED DESCRIPTION OF THE INVENTION

Figure 1:
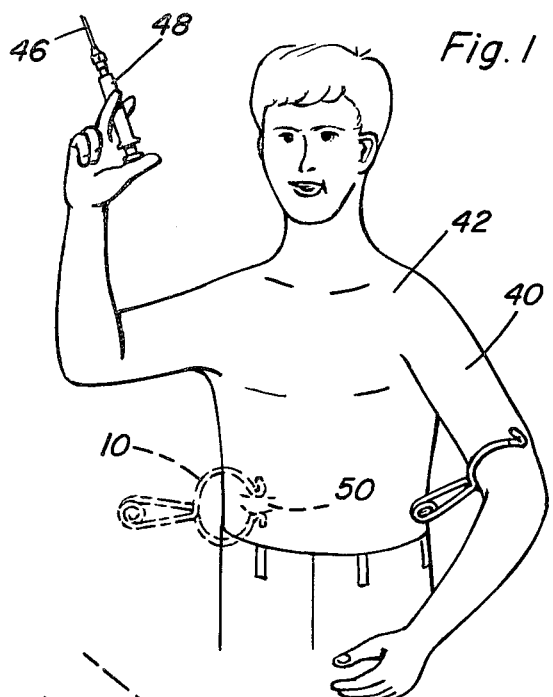
FIG. 1 is a perspective view illustrating the clamp of the instant invention engaged with the upper arm portion of a person preparing his upper arm portion as an injection site and with an alternate position of the clamp engaging the stomach of the person illustrated in phantom lines.
Figure 3:
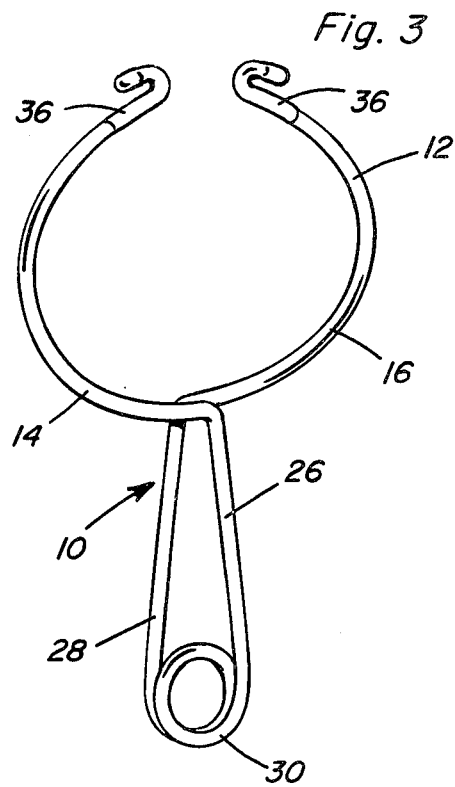
FIG. 3 is an enlarged perspective view of the clamp.
Figure 2:
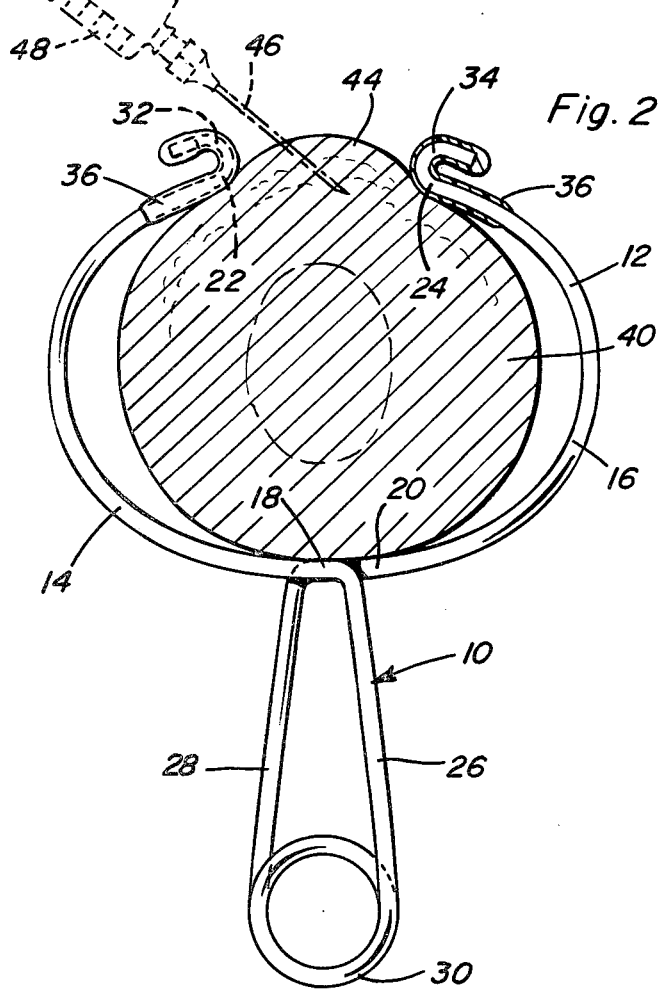
FIG. 2 is an enlarged sectional view taken substantially upon a plane passing through the arm portion engaged by the clamp as illustrated in FIG. 1.

Referring now more specifically to the drawings, the numeral 10 generally designates a first form of clamp constructed in accordance with the present invention. The clamp 10 is of one piece construction and is formed of a single piece of heavy gauge spring-metal wire 12. The wire 12 is formed into a pair of opposing semi-circular jaws 14 and 16 opening toward each other. The jaws 14 and 16 include a first pair of adjacent corresponding ends 18 and 20 and a second pair of corresponding adjacent ends 22 and 24. Formed integrally with the ends 18 and 20 of the jaws 14 and 16 are a pair of generally parallel elongated arms 26 and 28 extending outwardly from the jaws 14 and 16 away from the ends 22 and 24 thereof. The ends of the arms 26 and 28 are interconnected by means of an integral coiled portion 30 of the wire 12. The coiled portion 30 is of approximately 540 degrees in angular extent and the coiled portion 30 tends to swing the ends of the arms 26 and 28 adjacent the jaws 14 and 16 away from each other, thereby moving the jaws 14 and 16 toward each other.

The ends 22 and 24 of the jaws 14 and 16 include out turned reversely curved terminal ends 32 and 34 and the terminal ends 32 and 34 as well as the adjacent portions of the jaws 14 and 16 are covered with a plastic coating 36.

In operation, the clamp 10 may be opened by squeezing the arms 26 and 28 toward each other thereby causing the jaws 14 and 16 to open. Thereafter, the clamp 10 is engaged about the arm 40 of the user 42 and the arms 26 and 28 may then be released whereby the curved portion 30 will tend to swing the ends of the arms 26 and 28 adjacent the jaws 14 and 16 away from each other to swing the jaws 14 and 16 into clamping engagement with the arm 40. That portion of the arm 40 received between the terminal ends 32 and 34 of the jaws 14 and 16 is indicated by the reference numeral 44 and is lightly pinched between the end portions 32 and 34. Thereafter, the needle 46 of a syringe 48 carried by the other hand of the user 42 may be advanced into the injection site 44 from substantially any angle. The end portions 22 and 24 of the jaws 14 and 16 are located only in small areas on opposite sides of the injection site 44 and, therefore, do not interfere with access to the injection site 44.

As an alternative, as illustrated in phantom lines in FIG. 1, the clamp 10 may be engaged with the fleshy portion 50 on the stomach of the user 42 whereby the portion 50 may also be prepared as an injection site.

Figure 4:
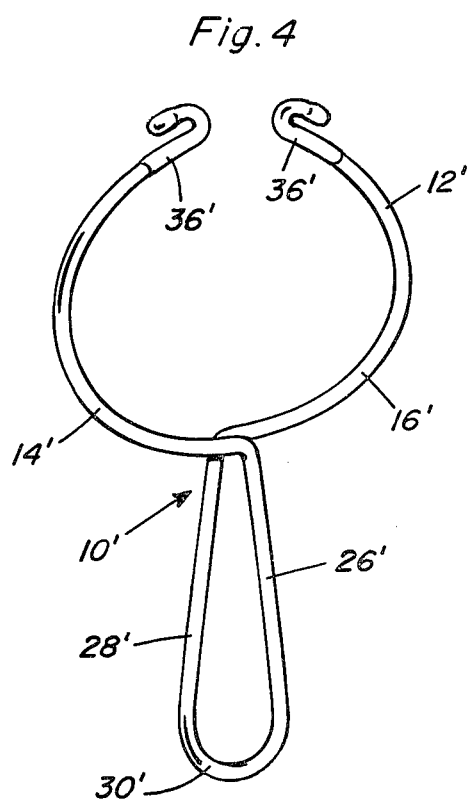
FIG. 4 is an enlarged perspective view of a slightly modified form of clamp.

With attention now invited more specifically to FIG. 4 of the drawings, there may be seen a modified form of clamp referred to in general by the reference numeral 10'. The clamp 10' is substantially identical to the clamp 10 and, therefore, has its major components indicated by prime reference numerals corresponding to the reference numerals designating the similar components of the claim 10. The clamp 10' differs from the clamp 10 only in that the curved portion 30' thereof is of only 180 degrees angular extent as opposed to 540 degrees angular extent. Otherwise, the operation of the clamp 10' is identical to the operation of the clamp 10.

In addition to the end portions 22 and 24 of the clamp 10 and the corresponding components of the clamp 10' providing substantially totally free access to an associated injection site, the end portions 22 and 24 even if they should slip across the injection site 44, do not contaminate the entire injection site 44 and the clamp 10 may be reapplied and the self injection by the user 42 may be continued without repreparing the injection site in order to render it sterile. Some forms of previously known clamps include wide jaws and the utilization of such wide jaws results in the entire injection site being contaminated should such wide jaws slip across the injection site when the clamp is applied to the user's arm. Further, other forms of injection site clamps are used to pinch the outer layer of skin and to pull the outer layer of skin out from the remainder of the arm. This type of clamp is not only sometimes painful to utilize but cannot be utilized efficiently on persons whose flesh is reasonably firm. Still further some forms of previously known injection site clamps are complicated to apply while others do not have the ability to compensate for arm sizes which are different. An arm injection site clamp which may not readily compensate for slightly different sizes of arm areas may not be utilized, in many instances, on different areas of the same arm. Accordingly, persons utilizing arm clamps which may not readily compensate for different size arm areas tend to develop more serious and more definitely localized scar tissue from repeated injections. However, it may be noted from the clamps 10 and 10' that they are readily adaptable to slightly different size arm areas. Accordingly, the clamps 10 and 10' may be utilized readily, in a manner to prepare an injection site without obscuring the injection site from any angle, on arms with firm flesh and without contamination of the entire injection site in the event the clamp slips.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. An injection site clamp comprising a pair of substantially semi-circular opposing jaws constructed of heavy gauge spring wire and disposed in closely spaced parallel planes, said jaws including first and second pairs of corresponding ends and being adapted to clampingly engage an arm portion therebetween, said first pair of corresponding ends terminating in a pair of generally parallel arm portions extending outwardly from said first ends in a direction extending away from said second ends, and spring means interconnecting the outer ends of said arms yieldingly biasing the ends of said arms from which said jaws are supported in directions to swing said jaws toward each other, said second pair of ends of said jaws including integral reversely curved and outwardly directed terminal ends adapted to lightly squeezably engage opposite remote side portions of a flesh injection site therebetween.

2. The combination of claim 1 wherein said clamp comprises a single, formed, piece of heavy gauge spring wire and, said spring means comprising a curved section of said single piece of wire, said curved section being of generally 180 degrees angular extent.

3. The combination of claim 1 wherein said clamp comprises a single, formed, piece of heavy gauge spring wire and, said spring means comprising a curved section of said single piece of wire, said curved section being of generally 540 degrees angular extent.

4. The combination of claim 1 wherein said terminal ends and the adjacent portions of said second ends include a thin coating of resilient material.

* * * * *